United States Patent
Körfer et al.

(10) Patent No.: US 6,797,827 B2
(45) Date of Patent: Sep. 28, 2004

(54) PROCESS FOR THE PREPARATION OF ALPHA-AMINO ACIDS BY HYDROLYSIS OF HYDANTOINS AT ELEVATED PRESSURE AND ELEVATED TEMPERATURE

(75) Inventors: Martin Körfer, Kalmthout-Achterbroek (BE); Dieter Buss, Hamburg (DE); Horst Weigel, Rodenbach (DE); Christoph Weckbecker, Gründau-Lieblos (DE); Hans Joachim Hasselbach, Gelnhausen (DE); Klaus Huthmacher, Gelnhausen (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/630,094

(22) Filed: Jul. 30, 2003

(65) Prior Publication Data

US 2004/0039228 A1 Feb. 26, 2004

(30) Foreign Application Priority Data

Aug. 21, 2002 (DE) .......................................... 102 38 212

(51) Int. Cl.⁷ ............................................ C07D 233/86

(52) U.S. Cl. ..................................................... 548/318.5
(58) Field of Search ....................................... 548/318.5

(56) References Cited

U.S. PATENT DOCUMENTS 2,557,920 A    6/1951   White

FOREIGN PATENT DOCUMENTS

| FR | 27 85 609 A1 | 5/2000 |
|----|--------------|--------|
| JP | 03 95145 A   | 4/1991 |
| JP | 03-95146 A   | 4/1991 |
| JP | 03 095146 A  | 4/1991 |

*Primary Examiner*—Alton N. Pryor
(74) *Attorney, Agent, or Firm*—Smith, Gambrell & Russell, LLP

(57) ABSTRACT

A process for the preparation of α-amino acids by hydrolysis of hydantoins in the presence of water and at least one metallic oxide under conditions such that all the starting materials are completely dissolved in the water as a result of high pressure and high temperature and only one further phase is present in the reactor in addition to the metallic oxide phase.

22 Claims, No Drawings

PROCESS FOR THE PREPARATION OF ALPHA-AMINO ACIDS BY HYDROLYSIS OF HYDANTOINS AT ELEVATED PRESSURE AND ELEVATED TEMPERATURE

INTRODUCTION

The present invention relates to a process for the preparation of α-amino acids by hydrolysis of hydantoins in the presence of water and of at least one metallic oxide under conditions such that all the starting materials are completely dissolved in the water as a result of high pressure and high temperature and only one further phase is present in the reactor in addition to the solid phase of the metallic oxide.

BACKGROUND PRIOR ART

It is known from U.S. Pat. No. 2,557,920 that α-amino acids are formed by saponification of hydantoins using sodium hydroxide. However, such processes require at least 3 moles of sodium hydroxide per mole of hydantoin. The same is true when potassium hydroxide is used.

DE 19 06 405 describes the hydrolysis of 5-(2-methylmercaptoethyl)-hydantoin using an aqueous solution of alkali carbonate and/or alkali hydrogen carbonate. During the hydrolysis, ammonia and carbon dioxide are constantly removed. Of the alkali carbonates, potassium carbonate is preferred; a molar ratio of hydantoin to alkali of from 1:1 to 1:5 is used. The hydrolysis is carried out under pressure at from 120 to 220° C. The alkali methioninate solution is used to liberate D,L-methionine with carbon dioxide; the mother liquor from the separation of the methionine that has crystallized out is used again in the circuit for the hydantoin hydrolysis, optionally with the discharge of from 1 to 2%.

Processes for the preparation of α-amino acids from hydantoins without the simultaneous production of salts are described in JP 03-95 145A and in JP 03-95146A. In those processes, the hydantoins are saponified, with the addition of water and catalysts consisting of metallic oxides (e.g. $TiO_2$, $ZrO_2$), at temperatures from 80 to 220° C. with elimination of ammonia. This is carried out discontinuously over a period of from 10 minutes to 10 hours in a stirred autoclave in which there is established a pressure corresponding approximately to the vapour pressure of water at the temperature which has been set. Accordingly, there are at least two phases in the autoclave: a liquid phase and a gas phase.

The processes described in JP 3-95145A and JP 3-95146A, which are carried out batchwise or continuously, lead, with the described dwell times, to the formation of numerous by-products in relatively high concentrations. Yields of max. 69% are mentioned for the preparation of methionine.

Another method for the continuous preparation of methionine without the preparation of a salt as by-product is described in FR-A 27 85 609.

Starting from the amino nitrile of methionine, which is hydrated, with the addition of a ketone (acetone) as homogeneous catalyst, to methionine amide at from 10 to 40° C., the methionine amide so obtained is hydrolyzed to methionine at from 100 to 180° C. A further possible method of carrying out that hydrolysis consists in a heterogeneously catalyzed reaction at about 100° C. and 1 bar, in which catalysts selected from $TiO_2$, $TiO_2/Al_2O_3$, $Nb_2O_5$, $Nb_2O_5$—$Al_2O_3$, ZnO and $ZrO_2$ can be used. The ammonia formed during the reaction is removed in that process.

The necessary addition of a ketone for the saponification of the amino nitrile of methionine to methionine amide requires further expensive working-up steps.

SUMMARY OF THE INVENTION

An object of the invention is to provide a process for the preparation of α-amino acids in which hydantoins are saponified without the formation of waste salts, and the α-amino acids are obtained in a high yield.

The present invention provides a process for the preparation of α-amino acids by hydrolysis of hydantoins of the general formula

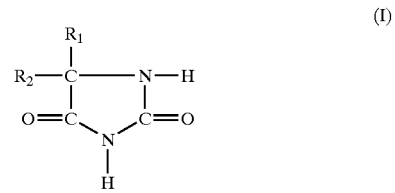

(I)

in which

R₁, R₂: which may be identical or different, and represent hydrogen, alkyl having from 1 to 6 carbon atoms, especially methyl, ethyl, propyl, straight-chain or branched chain; or alkylene radicals having from 1 to 6 carbon atoms which are closed to form a ring when R₁ and R₂ represent alkylene; or, when R₁ or R₂ represents alkylene, are bonded to methylthio, mercapto, hydroxyl, methoxy, amino groups or halogen atoms, especially fluorine or chlorine, R₁ or R₂: represents a phenyl group which is optionally substituted by methyl, hydroxyl groups or halogens, especially fluorine or chlorine, in the presence of water, ammonia and at least one metallic oxide as catalyst, selected from the group consisting of $TiO_2$, $TiO_2/Al_2O_3$, $Nb_2O_5/Al_2O_3$, ZnO and $ZrO_2$, in a saponification reactor under conditions in which all the starting materials are completely dissolved in the water and only one further phase is present in the reactor in addition to the solid phase of the metallic oxide.

The terms alkylene or alkylene radical mean to a divalent saturated hydrocarbon radical.

R₁ and R₂ preferably represent:

R1 hydrogen,

R2 isopropyl, 2-methylpropyl, phenyl or hydrogen, so that valine, leucine, phenylalanine or glycine are formed from the hydantoins by saponification.

Particular preference is given to the hydantoin in which R₁ or R₂ represents hydrogen and R₂ or R₁ represents the 2-methylthioethyl radical, so that methionine is prepared as the product.

DETAILED DESCRIPTION OF INVENTION

The reaction (hydrolysis, saponification) is generally carried out at a temperature of from 120 to 250° C., preferably from 150 to 210° C., and a pressure of from 80 to 300 bar, especially from 110 to 200 bar. Under those conditions, the reaction mixture (hydrolysis mixture) is in a state in which the interface between the liquid phase and the gaseous phase disappears.

Reaction-slowing transport resistances at phase boundaries other than the surfaces of the solid oxides are accordingly no longer present.

This is manifested by a short reaction time, which is generally in a range of from 10 to 120 seconds, especially from 20 to 80 seconds.

The hydrolysis is generally carried out in the presence of from 5 to 40 moles of $NH_3$, especially from 25 to 35 moles, based on moles of hydantoin.

In a preferred embodiment, the hydantoin-containing solution fed into the reactor already contains carbon dioxide in an amount of from >0 to 10 wt. %, particularly from 0.2 to 7 wt. %, especially from 0.4 to 5 wt. %, based on the total amount of solution.

Ammonia or a gaseous ammonia/water mixture is generally fed into the saponification reactor or reaction zone at a temperature of from 180 to 500° C., preferably from 210 to 360° C., and a pressure of from 80 to 300 bar, especially from 110 to 200 bar, as is the above-mentioned hydantoin-containing solution, which optionally contains $CO_2$.

The ammonia/water mixture generally consists of from 5 to 50 wt. %, especially from 2.5 to 40 wt. %, ammonia, the remainder consisting of water.

The hydantoins are generally present in the hydrolysis mixture in a concentration of from 150 to 600 g/l, especially from 200 to 450 g/l.

Ammonia or an ammonia/water mixture is preferably mixed with the hydantoin- and optionally carbon dioxide-containing solution, and the mixture is then fed into the reactor, with the desired pressures and temperatures, as mentioned above, being established (hydrolysis mixture).

Any suitable reactor can be used for purposes of the invention.

In general, in order to prepare that mixture, the hydantoin-containing solution at a temperature of from 20 to 80° C. and at from 80 to 300 bar, especially from 110 to 200 bar, is mixed with an ammonia/water mixture that is at from 180° C. to 500° C. and from 110 to 200 bar, especially from 130 to 200 bar, so that the desired reaction temperature and the desired pressure are established when the mixture is fed into the reactor.

The hydantoin-containing solution preferably originates from the reaction mixtures obtained after synthesis and preferably already contains carbon dioxide.

The oxidic catalyst is used in various forms, either in powder form, shaped in the conventional manner or in the form of a fixed bed.

It has been found that $TiO_2$ in the crystalline form anatase is particularly suitable.

In general, the chosen catalyst is used in an amount of from >0 to 0.1 kg, preferably from 0.001 to 0.05 kg, based on 1 kg of the hydantoin used.

Following the saponification of the hydantoin, which is carried out continuously or batchwise, ammonia and carbon dioxide are separated from the liquid phase in a suitable apparatus with a portion of the water in vapour form.

The portion of the water/ammonia/carbon dioxide mixture formed in the saponification reaction is preferably returned to the hydantoin synthesis or fed to the saponification process again in the desired amount.

The aqueous mixture obtained after separation generally contains from 10 to 40 wt. %, based on the total amount, of the desired α-amino acid.

The α-amino acid is crystallized out by known means and separated from the mother liquor.

The mother solution containing as yet unreacted hydantoins is returned to the hydrolysis process and mixed with fresh hydantoin-containing solution upstream of the reactor. The mother solution generally accounts for more than about 30 vol. % of the reaction mixture, which contains a corresponding amount of fresh hydantoin-containing solution. In order to avoid the concentration of any by-products which may be present, from 1 to 2 vol. % of the mother liquor are generally discharged.

In the process according to the invention it is possible, especially also when preparing methionine, to use mixtures that contain up to 10 wt. % of by-products from the hydantoin synthesis, without any loss in yield.

EXAMPLES

Example 1

A solution heated to 60° C. and containing 20 wt. % 5-(2-methylmercaptoethyl)-hydantoin and 3 wt. % $CO_2$ in water, which solution contains a considerable amount of impurities in the form of 5-(2-methylmercaptoethyl)-hydantoic acid and 5-(2-methylmercaptoethyl)-hydantoic acid amide, methionine amide, methionine nitrile and meth-ylmercaptopropionaldehyde cyanhydrin, imino nitrile and polymers, is continuously mixed, in a ratio of 4:7, at a pressure of 150 bar, with a solution heated to 250° C. and consisting of 25 wt. % ammonia and 75 wt. % water. This mixture then has a temperature of about 180° C. and is introduced into a reactor which has been adjusted to a temperature of 180° C. and is filled with catalyst. The catalyst consists of $TiO_2$ in the crystalline form anatase. The dwell time of the reaction mixture inside the reactor is set at 70 seconds. The liquid product mixture so obtained contains, downstream of the reactor, about 4.1 wt. % methionine, 4.9 wt. % methionine amide and 1.9 wt. % unreacted 5-(2-methylmercaptoethyl)-hydantoin. The molar yield of methionine, based on the amounts of 5-(2-methylmercaptoethyl)-hydantoin entering the reactor, is more than 63%. Downstream of the reactor, the pressure of the solution is brought to ambient pressure, and water, $CO_2$ and ammonia are partially separated off. The methionine is crystallized out from the resulting mother liquor and filtered off. The purity of the separated and dried methionine is greater than 95%.

Example 2

The procedure of Example 1 was followed, but the temperature of the ammonia/water mixture was set at 200° C. and the temperature in the reactor was set at 145° C. The liquid product mixture so obtained contains, downstream of the reactor, about 2.3 wt. % methionine, 2.2 wt. % methionine amide and 5.2 wt. % unreacted 5-(2-methylmercaptoethyl)-hydantoin. The molar yield of methionine, based on the amounts of 5-(2-methylmercaptoethyl)-hydantoin entering the reactor, is more than 35%.

Example 3

The procedure of Example 1 was followed, but the temperature of the ammonia/water mixture was set at 300° C. and the temperature in the reactor was set at 210° C. The liquid product mixture so obtained contains, downstream of the reactor, about 2.9 wt. % methionine, 0.5 wt. % methionine amide and 0.1 wt. % unreacted 5-(2-methylmercaptoethyl)-hydantoin. The molar yield of methionine, based on the amounts of 5-(2-methylmercaptoethyl)-hydantoin entering the reactor, is more than 45%.

Example 4

A solution (starting material) heated to 60° C. and containing 19.5 wt. % 5-(2-methylmercaptoethyl)-hydantoin and 2.8 wt. % $CO_2$ in water, which solution contains a considerable amount of impurities in the form of 5-(2-methylmercaptoethyl)-hydantoic acid and 5-(2- methylmercaptoethyl)-hydantoic acid amide, methionine amide, methionine nitrile and methylmercaptopropionaldehyde cyanhydrin, imino nitrile and polymers, is continuously mixed, in a ratio of 1:1, at a pressure of 150 bar, with a solution heated to 305° C. and consisting of 29 wt. % ammonia and 71 wt. % water. This mixture then has a temperature of 180° C. and is introduced into a reactor which has been adjusted to a temperature of 180° C. and is filled with catalyst. The catalyst consists of $TiO_2$ in the crystalline form anatase. The dwell time of the reaction mixture inside the reactor is set at 80 seconds. The liquid product mixture so obtained contains, downstream of the reactor, about 3.4 wt. % methionine, 4.8 wt. % methionine amide and 6.0 wt. % unreacted 5-(2-methylmercaptoethyl)-hydantoin. The molar yield of methionine, based on the amounts of 5-(2-methylmercaptoethyl)-hydantoin entering the reactor, is more than 40%. Downstream of the reactor, the pressure of the solution is brought to ambient pressure, and water, $CO_2$ and ammonia are partially separated off. The methionine is crystallized out from the resulting mother liquor and filtered off. The purity of the separated and dried methionine is greater than 85.5%.

The filtrate that remains is mixed with fresh starting material in a ratio of 10:3. A portion of the ammonia/$CO_2$/water mixture previously separated off is compressed at 150 bar again and heated to 320° C. and fed into the mixture of filtrate and starting material at 150 bar.

That mixture is again introduced into the reactor adjusted to a temperature of 180° C. and filled with catalyst, the temperature and the dwell time corresponding to those of the first pass. The liquid product mixture so obtained contains, downstream of the reactor, about 3.7 wt. % methionine, 4.3 wt. % methionine amide and 3.8 wt. % unreacted 5-(2-methylmercaptoethyl)-hydantoin. The molar yield of methionine, based on the amounts of 5-(2-methylmercaptoethyl)-hydantoin entering the reactor, is more than 73%.

Downstream of the reactor, water, $CO_2$ and ammonia are partially separated off again and the pressure of the solution is brought to ambient pressure. The methionine is crystallized out from the resulting mother liquor and filtered off. The purity of the separated and dried methionine is greater than 85.1%.

Further modifications and variations of the foregoing will be apparent to those skilled in the art and are intended to be encompassed by the claims appended hereto.

German priority application 102 38 212.3 of Aug. 21, 2002 is relied on and incorporated herein by reference.

We claim:

1. A process for the preparation of an α-amino acid by a reaction comprising hydrolyzing a hydantoin of the formula

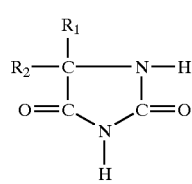

(I)

in which $R_1$, $R_2$: can be identical or different, and represent hydrogen, alkyl having from 1 to 6 carbon atoms, straight-chain or branched chain; or alkylene radicals having from 1 to 6 carbon atoms which are closed to form a ring when $R_1$ and $R_2$ taken together are alkylene or, when $R_1$ or $R_2$ represents alkylene, are bonded to methylthio, mercapto, hydroxyl, methoxy, amino groups or halogen atoms, or $R_1$ and $R_2$: can also be a phenyl group which is optionally substituted by methyl, hydroxyl groups or halogen atoms, in the presence of water, ammonia as starting materials and at least one metallic oxide as catalyst, selected from the group consisting of $TiO_2$, $TiO_2/Al_2O_3$, $Nb_2O_5/Al_2O_3$, ZnO and $ZrO_2$, in a saponification zone under conditions in which all starting materials are completely dissolved in the water and only one further phase is present in the reactor in addition to the solid phase of the metallic oxide.

2. The process according to claim 1, wherein the reaction is carried out at a temperature of from 120 to 250° C. and a pressure of from 80 to 300 bar (250,000 hPas) in the presence of carbon dioxide.

3. The process according to claim 1, wherein the ammonia, optionally in the form of a water/ammonia mixture, is mixed in an amount of from 5 to 40 moles $NH_3$, based on moles of hydantoin, with the hydantoin-containing solution and fed into the saponification zone.

4. The process according to claim 1 wherein said halogen atoms are selected from the group consisting of fluorine and chlorine.

5. The process according to claim 2, wherein the ammonia, optionally in the form of a water/ammonia mixture, is mixed in an amount of from 5 to 40 moles $NH_3$, based on moles of hydantoin, with the hydantoin-containing solution and fed into the saponification zone.

6. The process according to claim 1, further comprising feeding a water/ammonia mixture or a hydantoin-containing solution optionally containing ammonia and optionally containing carbon dioxide into the saponification zone under pressure at a temperature of from 180 to 500° C.

7. The process according to claim 3, further comprising feeding a water/ammonia mixture or a hydantoin-containing solution optionally containing ammonia and optionally containing carbon dioxide into the saponification zone under pressure at a temperature of from 180 to 500° C.

8. The process according to claim 1, wherein $R_1$ corresponds to hydrogen and $R_2$ corresponds to the isopropyl, 2-methylpropyl or phenyl radical or hydrogen.

9. The process according to claim 1, wherein $R_1$ corresponds to hydrogen and $R_2$ corresponds to a methylmercaptoethyl radical.

10. The process according to claim 1, wherein the hydantoin is present in the hydrolysis mixture in a concentration of from 150 to 600 g/l.

11. The process according to claim 1, wherein the catalyst is $TiO_2$ in the crystalline form anatase.

12. The process according to claim 1, wherein the metallic oxide is in the form of a fixed bed.

13. The process according to claim 1, wherein the catalyst is present in an amount of from >0 to 0.1 kg, based on 1 kg of hydantoin.

14. The process according to claim 1, wherein the process is carried out continuously, semi-continuously or discontinuously.

15. The process according to claim 1, further comprising following saponification, lowering the pressure, during the discharge from the saponification zone of a mixture obtained after the hydrolysis, separating ammonia and carbon dioxide, together with water vapour, from a liquid phase as a separated liquid phase.

16. The process according to claim 15, further comprising optionally returning to the hydantoin synthesis amounts of ammonia and carbon dioxide formed in the hydrolysis reaction.

17. The process according to claim 15 further comprising feeding a remainder of the ammonia and carbon dioxide into the saponification zone at a temperature of from 180 to 500° C., and a pressure of from 80 to 300 bar.

18. The process according to claim 15 wherein the α-amino acid is isolated from said separated liquid phase.

19. The process according to claim 17 wherein a remaining portion containing unreacted hydantoin is mixed with fresh hydantoin-containing solution upstream of the saponification zone, and is fed into the saponification zone.

20. The process according to claim 17 wherein the temperature is 210° to 360° C.

21. The process according to claim 17 wherein the pressure is 110 to 200 bar.

22. The process according to claim 1, further comprising following saponification, lowering pressure, during the discharge from the saponification zone of the mixture obtained after the hydrolysis, separating ammonia and carbon dioxide, together with water vapour, from a liquid phase as a separated liquid phase, as a separated liquid phase, optionally returning to the hydantoin synthesis a portion corresponding to the amounts of ammonia and carbon dioxide formed in the hydrolysis reaction, feeding the remainder of the ammonia and carbon dioxide into the saponification zone at a temperature of from 180 to 500° C., and a pressure of from 80 to 300 bar, isolating said α-amino acid from said separated liquid phase, mixing the remaining portion containing unreacted hydantoin with fresh hydantoin-containing solution upstream of the saponification zone, and feeding it into the saponification zone.

* * * * *